(12) United States Patent
Voorhans et al.

(10) Patent No.: US 10,544,064 B2
(45) Date of Patent: Jan. 28, 2020

(54) FLUIDIZED BED GRANULATION

(71) Applicant: Yara International ASA, Oslo (NO)

(72) Inventors: Jaap Voorhans, Terneuzen (NL);
André Kayaert, Sluiskil (NL); Luc Vanmarcke, Sluiskil (NL)

(73) Assignee: YARA INTERNATIONAL ASA, Oslo (NO)

( * ) Notice: Subject to any disclaimer, the term of this patent is extended or adjusted under 35 U.S.C. 154(b) by 466 days.

(21) Appl. No.: 14/925,470

(22) Filed: Oct. 28, 2015

(65) Prior Publication Data
US 2016/0115089 A1  Apr. 28, 2016

(30) Foreign Application Priority Data

Oct. 28, 2014 (NL) .................................. 2013694

(51) Int. Cl.
| | |
|---|---|
| *C05C 1/02* | (2006.01) |
| *C05C 9/00* | (2006.01) |
| *C05G 3/00* | (2006.01) |
| *B01J 2/16* | (2006.01) |
| *C07C 273/02* | (2006.01) |
| *C01C 1/18* | (2006.01) |

(52) U.S. Cl.
CPC .............. *C05C 1/02* (2013.01); *B01J 2/16* (2013.01); *C01C 1/185* (2013.01); *C05C 9/00* (2013.01); *C05G 3/0058* (2013.01); *C07C 273/02* (2013.01)

(58) Field of Classification Search
None
See application file for complete search history.

(56) References Cited

U.S. PATENT DOCUMENTS

| | | | |
|---|---|---|---|
| 4,219,589 A * | 8/1980 | Niks | B01J 2/16 |
| | | | 159/45 |
| 5,120,345 A * | 6/1992 | Kayaert | B01J 2/16 |
| | | | 71/30 |
| 5,779,945 A | 7/1998 | Nijsten | |
| 2006/0123602 A1† | 6/2006 | Eygelaar | |
| 2008/0148594 A1* | 6/2008 | Waldron | F26B 3/08 |
| | | | 34/384 |

(Continued)

FOREIGN PATENT DOCUMENTS

| | | |
|---|---|---|
| CN | 103664240 | 3/2014 |
| CN | 102964148 B † | 7/2014 |

(Continued)

OTHER PUBLICATIONS

Search Report for corresponding foreign application NL 2013694, filed Oct. 28, 2014.

(Continued)

*Primary Examiner* — Mary Lynn F Theisen
(74) *Attorney, Agent, or Firm* — Arent Fox LLP

(57) ABSTRACT

Method and fluidized bed reactor for the production of granules, such as granules of urea or ammonium nitrate. The reactor comprises at least one granulation compartment with air inlets, and an air moving device downstream the granulation compartment, e.g., downstream one or more scrubbers. The air moving device is configured to draw air through said one or more air inlets into the granulation compartment.

12 Claims, 1 Drawing Sheet

(56) References Cited

U.S. PATENT DOCUMENTS

| | | | |
|---|---|---|---|
| 2012/0187223 A1 | 7/2012 | Meessen | |
| 2013/0344239 A1* | 12/2013 | Bedetti | C05C 9/005 427/213 |
| 2015/0217221 A1 | 8/2015 | Wang | |
| 2015/0217248 A1 | 8/2015 | Wang | |
| 2015/0283527 A1* | 10/2015 | Alt | A23K 40/10 264/5 |

FOREIGN PATENT DOCUMENTS

| | | | |
|---|---|---|---|
| DE | 102 60 740 A1 | | 7/2004 |
| EP | 0900589 A1 | † | 3/1999 |
| EP | 2253374 | | 5/2009 |
| JP | 2002172320 A | † | 6/2002 |
| JP | 2009056434 A | † | 3/2009 |
| JP | 2013188728 A | † | 9/2013 |
| NL | 2009295 | | 2/2014 |
| NL | 2009297 | | 2/2014 |
| WO | WO 02/057005 A1 | | 7/2002 |

OTHER PUBLICATIONS

Niehues et al., "Yara's well established Fluid Bed Granulation now at the Uhde Fertilizer Technology," Uhde Fertiliser Symposium 2006 Dortmund, Germany—May 17-19, 2006, pp. 1-8.

\* cited by examiner
† cited by third party

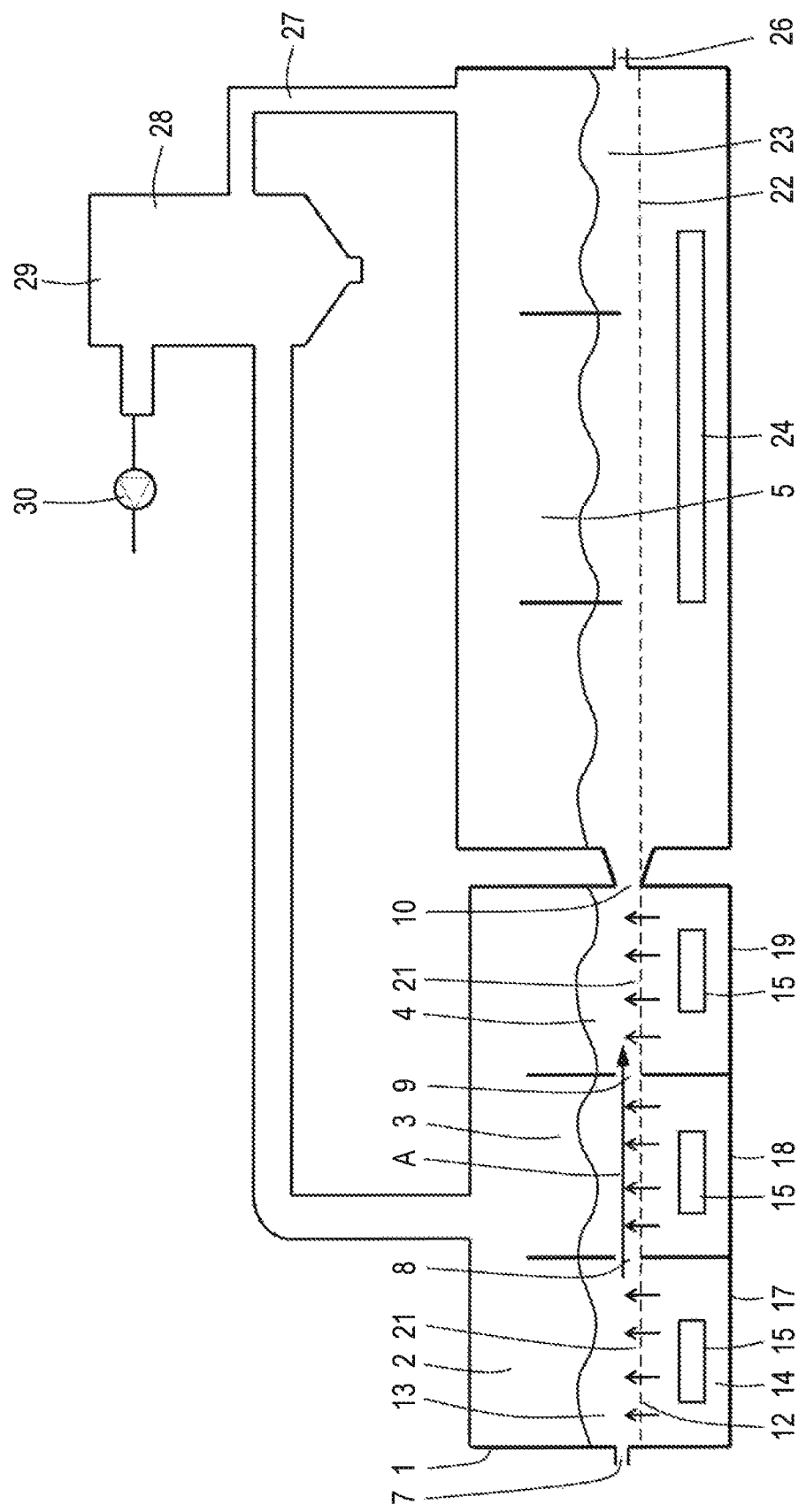

FLUIDIZED BED GRANULATION

BACKGROUND

The discussion below is merely provided for general background information and is not intended to be used as an aid in determining the scope of the claimed subject matter.

Aspects of the invention relate to a fluidized bed reactor and a method for the production of granules, such as granules of urea or ammonium nitrate, typically used as a fertilizer material.

TECHNOLOGICAL BACKGROUND

To produce urea granules a urea liquid, such as an aqueous or non-aqueous urea solution, is sprayed into a granulation compartment containing a fluidized bed of solid nuclei. The fluidized bed is fluidized by blowing a fluidization gas, usually air, through the bed of nuclei. The nuclei grow by solidification and crystallization of the sprayed urea liquid on them, to form granules of a desired average size. NL 2009295 and NL 2009297 disclose examples of such a fluidized bed reactor for the production of urea granules.

The fluidization air is generally blown into the granulation compartments by means of blowers. In a next compartment the air is stripped, e.g., in a scrubber, a cyclone or a similar separator. The air is usually removed from the granulation reactor by means of an exhaust fan.

The produced granules are generally moved from the granulation compartment to an after-cooler. In the after-cooler further dust is produced. Therefore, also air from the after-cooler is usually first treated in a scrubber before it can be vented.

To avoid leakage of air from the reactor a moderate vacuum, typically below, 10 mbar is usually created in the granulator compartment, as for instance is disclosed in U.S. Pat. No. 5,779,945 and EP 2 253 374 A1.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

It is an object of the invention to improve process efficiency while reducing energy consumption.

The object of the invention is achieved with a fluidized bed reactor comprising at least one granulation compartment with one or more air inlets, and one or more air moving devices downstream the granulation compartment configured to draw air through the one or more air inlets into the granulation compartment. To this end the downstream air moving devices have a capacity to generate a vacuum in the granulation compartment exceeding the total pressure drop between the air inlets and the downstream air moving devices. For instance the one or more air moving devices may be configured to create a vacuum of at least about 50 mbar, e.g., within the range of about 50 to about 70 mbar.

Where prior art systems use blowers to blow air into the granulation compartment, it was surprisingly found that drawing air by a downstream air moving device (e.g. air pump or fan) consumes substantially less energy, since the reactor can now be designed for lower inlet temperatures of the fluidization air.

Heat is generated during crystallization of the urea liquid collected on the solid nuclei. Air used for fluidization removes excess heat from the fluidized bed. The required amount of fluidization air depends on the temperature of the air entering the granulator compartment. If the fluidization air is warmer, more fluidization air is required to remove excess heat from the granulation compartment. As a result, more air has to be cleaned in the scrubbers and more power is consumed by the exhaust fans. Therefore, the temperature of the fluidization air should not be too high. If the temperature of the fluidization air is low, less air is required for cooling the fluidized bed. However, the inflow of fluidization air must not be too low, otherwise the bed of nuclei will not be sufficiently fluidized. Hence, the fluidized bed reactor should be designed in such a way that, on the one hand, the amount of fluidization air must be sufficient to achieve good fluidization and to cool the fluidized bed effectively, while, on the other hand, energy consumption for cleaning and discharging exhaust air should be minimized.

Air used for fluidization may for example be ambient air. The temperature of ambient air may differ considerably. The reactor is therefore usually designed for use with air of summer temperatures. With prior art systems these temperatures are increased with about 5-9° C. or even more because of the heat generated by the blowers. The blowers blowing the fluidization air into the granulation compartments generate heat. The generated heat is typically dependent on the efficiency of the used blower and on the pressure at the outlet of the blower. In practice, the generated heat is such that the passing air is heated by at least 5° C., normally at least 9° C., and sometimes 11° C. or more.

As a result, present day reactors are designed for use with relatively high temperatures of the fluidization air. This results in higher energy consumption by the blower, the scrubbers and the exhaust fans. Moreover, in winter, the ambient air should be pre-heated to bring it closer to the relatively high air temperature for which the reactor was designed.

With the reactor of the present invention, no blowers need to be used at the fluidization air inlet, but the air is drawn into the granulation compartment by means of at least one downstream air moving device. This means that the fluidization air is not heated by any blower and the reactor can be designed for lower inlet temperatures of the fluidization air. Less air needs to be consumed for cooling the fluidized bed and less air needs to be scrubbed and discharged. Moreover, lower pre-heating temperatures can be used in winter.

Using downstream air moving devices to draw air into the reactor also results in lower pressure in the granulation compartments. This in turn results in improved evaporation in the granulation compartments.

If an after-cooler is used, one or more air moving devices can, e.g., be positioned downstream the after-cooler. As a result the air entering the after-cooler is not heated by the air moving device motor, so it is already about 9-11° C. cooler when it enters the after-cooler. By eliminating the 9-11° C. heating of the fluidization air fan, the cooler can operate, e.g., with an ambient air temperature. This means a substantial improvement of the cooler capacity.

The after-cooler is generally also of the fluidized bed with a supply of fluidization air. The air moving device(s) downstream the after-cooler may be configured to draw fluidization air into the after-cooler, optionally into both the after-cooler and the granulation compartment.

The granulation compartment can for example be a spouted bed or any other suitable type of fluidized bed. Combinations of different types can also be used.

In a specific embodiment, the reactor may comprise one or more scrubbers downstream the one or more granulation compartments and/or downstream one or more after-coolers. In such a case the air moving device(s) for drawing fluidization air into the granulation compartment(s) may for example be downstream the one or more scrubbers. The air moving device may for example comprise one or more exhaust fans, in particular an exhaust of the scrubber.

A single scrubber can be used for scrubbing air from the after-cooler(s) and air from the granulation compartment(s).

Alternatively, a first scrubber with one or more downstream air moving devices can be used for the granulation compartments, while a second scrubber or set of scrubbers, with one or more downstream air moving devices can be used for the after-cooler.

The pressure drop over the scrubbers is preferably low. To this end, scrubbers may be used comprising vertical demisters. Particularly low pressure drop can be obtained by using a serial arrangement of a first demister for coarse particles (typically having a pressure drop of less than about 2 mbar) and a second demister for finer particles, e.g., submicron particles. If the air between the demisters is cooled condensation of moisture will enlarge the particles so the second demister can also be of a low pressure drop type. A suitable configuration of scrubbers is for example disclosed in US patent application US 2015/0217221, incorporated herein by reference in its entirety. Other configurations with or without scrubbers can also be used.

The invention also relates to a method for the production of granules, such as urea granules, using a fluidized bed reactor disclosed above. Fluidization air is sucked into the granulation compartment by the downstream air moving device, e.g., by creating a vacuum exceeding the pressure drop between the air inlets and the air moving devices. The vacuum may for instance be at least about 50 mbar, e.g., in the range of about 50 to about 70 mbar.

The fluidized bed reactor can for example be configured such that the pressure drop between the air inlets and the air exhaust is below 800 mm water column, preferably below 750 mm water column. The pressure drop over the granulation compartment may for example be 500 mm water column or less.

The temperature of the fluidization air entering the granulation compartment may for example be below 114° C., e.g., below 100° C., e.g., below 90° C. A spouted bed can for example be operated at or below 120° C.

The granulation compartments may further comprise a plurality of sprayers connected to a supply of a granulating liquid, such as an aqueous urea solution. The sprayers may for example be configured to spray the liquid in one or more spraying zones in the compartment next to one or more unsprayed zones. The sprayers can for example be atomizers or hydraulic sprayers, such as air-assisted hydraulic sprayers.

When the solution is sprayed into the granulator compartment, the solution may for instance have a temperature substantially above the crystallisation point. If the solution is a urea solution the solution can for instance be sprayed at a temperature of at least about 120° C., or at least about 130° C. or at least about 135° C. If the solution is an ammonium nitrate solution the solution can for instance be sprayed at a temperature of at least about 160° C., or at least about 170° C. or at least about 180° C. The solution can for example be sprayed under a hydrostatic pressure of 1.5-6 bar, e.g., 2-4 bar or other suitable pressures. The sprayed droplets can for example have an average droplet size of about 20-120 µm, e.g., about 30-60 µm.

For granulation of urea, highly concentrated solutions can be used, for example with a urea content of at least 90 wt % by total weight of the urea solution, e.g., at least 95 wt %.

The water content of the urea solution is generally low, e.g., less than 5 wt %, by total weight of the urea solution, e.g., less than 3 wt %. If the water content is less than 2.5 wt % the solution is often referred to as urea melt.

The urea solution may further contain additives such as for example formaldehyde and/or a urea-formaldehyde condensation products as a granulating aid for slowing down crystallisation of the urea and as an anti-caking agent preventing agglomeration of the resultant granules. If for instance 0.1 to 3%, based on total the weight of the urea solution, of formaldehyde is added to the urea aqueous solution, atomized liquid droplets adhere better to the urea nuclei. Other suitable additives can also be used.

For the granulation of ammonium nitrate, $Mg(NO_3)_2$ and aluminium sulphate, e.g., with NaOH are examples of suitable additives.

The nuclei can be supplied to the granulator via one or more inlets at an inlet side of the granulator. The nuclei can either be supplied continuously or be supplied and processed per batch.

Before being submitted to the granulation process, the nuclei may have any suitable average particle size, generally about at least 0.2, or at least 0.5 mm, generally at most 6 mm.

The nuclei may have any suitable composition. In general they will mainly comprise the same material as the crystallized granulating liquid, in particular crystallized urea, but is also possible to use nuclei of a different composition than the crystallized granulating liquid.

For granulating urea the flow velocity of the fluidization air in the fluidized bed can for example be about 1-8 m/sec, e.g., at least about 2 and/or at most about 3 or 4 m/sec. For granulating ammonium nitrate the flow velocity of the fluidization air in the fluidized bed can for example be about 1-8 m/sec, e.g., at least about 2 and/or at most about 3.5 or 4.5 m/sec.

For urea granulation the temperature in the compartments of the granulator can for instance be between 90-120° C., e.g., between 100-106° C. For granulation of ammonium nitrate the temperature in the compartments of the granulator can for instance be between 110-140° C., e.g., between 125-130° C. Typically, the temperature in the first compartment will be lower due to the return flow of recycled material. This can be compensated by using a higher density of sprayers in the first compartment.

To reduce the pressure drop over the granulation bed, the granulation bed may for example have a bed level of 1.5 m or less, e.g., about 1 m or less. Lower bed levels may reduce circulation of the granules in the fluidized bed. A suitable manner to reduce the bed level while maintaining the required circulation of granules is to use a granulator comprising one or more compartments with a floor with air inlet openings and a plurality of sprayers for spraying a granulating liquid, the sprayers being configured to spray the liquid in spraying zones next to unsprayed zones of the fluidized bed. The alternating arrangement of sprayed zones and unsprayed zones intensifies the required circulation of the granules and increases the residence time. Examples of such granulators are disclosed in US 2015/0217248, incorporated herein by reference in its entirety.

The processed granules are typically discharged via one or more outlets of the granulator, either continuously or per batch. The processed granules typically have an average particle size of about 2-4 mm, but can be made smaller or larger if so desired.

The water content of the granules can be kept well below 0.3 wt % by total weight of the granules, e.g., below 0.25 wt %.

Granules with a particle size above a given limit can be separated from the outflow. Optionally, these particles can be crushed and recycled to the granulator, e.g., together with granules with a particle size considered to be too small and/or with material separated from air discharged from the granulator.

The granulator can have one or more granulator compartments in a serial and/or parallel arrangement. In a specific embodiment, the granulator has at least two, e.g., three or more serially arranged compartments.

The inlets for fluidization air may for example comprise inlets in floors of the granulator compartments. To this end, the floor can for instance be a grid above an air supply.

Optionally, the granulator may comprise an after-cooler, such as a fluidized bed cooler receiving discharged granules from the granulator compartments. The after-cooler can for example be used to cool the granules to a temperature of about 40° C.

An exemplary embodiment of a granulator according to the invention will be explained under reference to the accompanying drawings.

BRIEF DESCRIPTION OF THE DRAWING

FIG. 1: shows a cross section along flow direction of an exemplary fluidized bed reactor.

DETAILED DESCRIPTION OF THE ILLUSTRATIVE EMBODIMENT

FIG. 1 shows an exemplary embodiment of a fluidized bed reactor 1 for the production of urea granules, or ammonium nitrate granules. The fluidized bed reactor 1 as shown in the FIGURE comprises three granulation compartments 2, 3, 4 for granulation and an after-cooler 5 for subsequent cooling and drying the granules.

The first granulation compartment 2 of the fluidized bed reactor 1 comprises an inlet 7 for the supply of nuclei. Opposite to the inlet 7 is a first passage 8, leading to the second compartment 3. The second compartment 3 comprises a second passage 9 opposite to the first passage 8 and leading to the third compartment 4. The third compartment 4 comprises an outlet 10 opposite to the second passage 9. As a result, the nuclei can flow from the inlet 7 to the outlet 10 in a straight flow path, indicated in FIG. 1 by arrow A.

The fluidized bed reactor 1 comprises a floor 12 made of a grid which supports a bed 13 of nuclei and which permits the passage of ambient fluidization air, supplied from a space 14 below the grid floor 12. Air inlets can for example be located at a side wall of the space 14 below the grid 12 and/or in the bottom of that space 14. In case the ambient air is relatively cold, for example during winter, the air is preheated by heaters 15 in or upstream the space 14. The heated air fluidizes the bed 13 of nuclei.

The space 14 below the grid floor 12 is divided into compartments 17, 18, 19 in line with the compartments 2, 3, 4 above the grid floor 12. In each of the compartments 2, 3, 4 the grid floor 12 of the fluidized bed reactor 1 is provided with clusters of air-assisted sprayers 21 projecting above grid floor 12. The sprayers 21 spray an aqueous solution of urea into the fluidized bed 13. In the granulator compartments 2, 3, 4 water of the sprayed urea solution evaporates and urea crystallizes on the nuclei, which grow to form granules.

The after-cooler 5 is a fluidized bed cooler with a grid floor 22 supporting a bed 23 of freshly produced granules and a space below the grid floor 22 with a heater 24 for the supply of air fluidizing and drying the bed 23.

The after-cooler 5 is provided with an outlet 26 for discharging the dried and cooled granules. Subsequently, undersize and oversize granules are separated from granules of the desired size, which are discharged for storage. The oversize granules can be crushed to finer particles, which can be recycled together with the undersize particles.

Air and air borne dust particles are discharged from the granulator compartments 2, 3, 4 and the after-cooler 5 via air ducts 27 to one or more wet scrubbers 28. In the schematic drawing of FIG. 1 a single scrubber is shown. Separate scrubbers may be used for treating air form the granulation compartments and air from the cooler, respectively, such as for instance is disclosed in NL 2009295.

In the scrubber 28 the air is stripped. Separated dust particles can be recycled to the granulator compartments 2, 3, 4. Clean air leaves the scrubber 28 via a discharge duct 29 comprising an exhaust fan 30.

The exhaust fan 30 creates a pressure drop of about 700-800, e.g., about 750 mm water column over the full flow path from the grid floor 12 to the exhaust fan 30. As a result fluidization air is sucked into the granulation compartments 2, 3, 4 via the grid floors 12. No additional blowers are provided.

In the embodiment of FIG. 1, the granulation compartments are at the same level as the cooler. The present invention is also suitable for use in other configurations, e.g., with the granulator being positioned below or above one or more after-coolers.

Although the subject matter has been described in language specific to structural features and/or methodological acts, it is to be understood that the subject matter defined in the appended claims is not necessarily limited to the specific features or acts described above as has been held by the courts. Rather, the specific features and acts described above are disclosed as example forms of implementing the claims.

What is claimed is:

1. A fluidized bed reactor comprising
   at least one granulation compartment with one or more air inlets;
   at least one scrubber downstream from the at least one granulation compartment;
   at least one air duct between the at least one granulation compartment and the at least one scrubber;
   and at least one air moving device downstream from the at least one granulation compartment,
   wherein when a fluid bed is present in the at least one granulation compartment, the at least one air moving device has or devices have sufficient capacity to create a vacuum exceeding the total pressure drop between the one or more air inlets and the at least one air moving device.

2. The fluidized bed reactor according to claim 1, wherein the at least one air moving device is downstream from the scrubber.

3. The fluidized bed reactor according to claim 1, further comprising at least one after-cooler downstream from the at least one granulation compartment.

4. The fluidized bed reactor according to claim 3, wherein the after-cooler is upstream from a scrubber and the at least one air moving device is positioned downstream from the scrubber.

5. The fluidized bed reactor according to claim 1, wherein the air moving device comprises one or more exhaust fans for discharging air.

6. A method for producing granules using a fluidized bed reactor comprising
- at least one granulation compartment having one or more air inlets and a bed of granules,
- at least one scrubber downstream from the at least one granulation compartment,
- at least one air duct between the at least one granulation compartment and the at least one scrubber, and
- at least one air moving device downstream from the at least one granulation compartment,
- the method comprising fluidizing the bed of granules by drawing air into the at least one granulation compartment through the one or more air inlets using the at least one air moving device,
- wherein the air drawn into the at least one granulation compartment is not heated by a blower upstream from the one or more air inlets.

7. The method of claim 6, wherein drawing air in the at least one granulation compartment includes creating a pressure drop between the one or more air inlets and an air exhaust below 800 mm water column.

8. The method of claim 7, wherein the pressure drop is below 750 mm water column.

9. The method according to claim 6, wherein the pressure drop over the granulation compartment is at most 500 mm water column.

10. The method according to claim 6, wherein the bed of granules include urea granules.

11. The method according to claim 6, wherein the bed of granules include ammonium nitrate granules.

12. A method for producing fertilizer granules by crystallization of urea and/or ammonium nitrate, using a fluidized bed reactor comprising
- at least one granulation compartment with one or more air inlets and a bed of granules,
- at least one scrubber downstream from the at least one granulation compartment,
- at least one air duct between the at least one granulation compartment and the at least one scrubber, and
- at least one air moving device downstream from the at least one granulation compartment,
- the method comprising fluidizing the bed of granules by drawing air into the at least one granulation compartment through the one or more air inlets using the at least one air moving device,
- wherein the air drawn into the at least one granulation compartment is not heated by a blower upstream from the one or more air inlets.

* * * * *